(12) United States Patent
MacLachlan et al.

(10) Patent No.: US 9,005,654 B2
(45) Date of Patent: Apr. 14, 2015

(54) SYSTEMS AND METHODS FOR MANUFACTURING LIPOSOMES

(75) Inventors: Ian MacLachlan, Mission (CA); Lloyd B. Jeffs, Delta (CA); Edward Yaworski, Maple Ridge (CA); Kieu Lam, Surrey (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 1247 days.

(21) Appl. No.: 11/495,150

(22) Filed: Jul. 27, 2006

(65) Prior Publication Data

US 2007/0042031 A1    Feb. 22, 2007

Related U.S. Application Data

(60) Provisional application No. 60/703,380, filed on Jul. 27, 2005.

(51) Int. Cl.
*A61K 9/127* (2006.01)
*A61K 31/7088* (2006.01)
*A61K 48/00* (2006.01)

(52) U.S. Cl.
CPC .............. *A61K 9/127* (2013.01); *A61K 9/1277* (2013.01); *A61K 31/7088* (2013.01); *A61K 48/00* (2013.01); *A61K 48/0025* (2013.01)

(58) Field of Classification Search
CPC ...................................................... A61K 9/127
USPC ......................................................... 424/450
See application file for complete search history.

(56) References Cited

U.S. PATENT DOCUMENTS

| | | | |
|---|---|---|---|
| 4,687,661 A | 8/1987 | Kikuchi et al. | |
| 5,424,073 A | 6/1995 | Rahman et al. | |
| 5,478,860 A | 12/1995 | Wheeler et al. | |
| 5,552,157 A | 9/1996 | Yagi et al. | |
| 5,653,996 A | 8/1997 | Hsu | |
| 5,885,613 A | 3/1999 | Holland et al. | |
| 5,976,567 A | 11/1999 | Wheeler et al. | |
| 5,981,501 A | 11/1999 | Wheeler et al. | |

(Continued)

FOREIGN PATENT DOCUMENTS

| CA | 2041075 A1 | 10/1991 |
|---|---|---|
| CA | 2427640 A1 | 5/2003 |

(Continued)

OTHER PUBLICATIONS

Hirota et al Biotechniques, vol. 27, # 2 (1990).*

(Continued)

*Primary Examiner* — Gollamudi Kishore
(74) *Attorney, Agent, or Firm* — Kilpatrick, Townsend & Stockton LLP

(57) ABSTRACT

The present invention provides apparatus and processes for producing liposomes. By providing a buffer solution in a first reservoir, and a lipid solution in a second reservoir, continuously diluting the lipid solution with the buffer solution in a mixing chamber produces a liposome. A therapeutic agent, such as nucleic acid, is included in one of the buffer solution or the lipid solution. Upon mixing a liposome encapsulating the therapeutic product is substantially instantaneously formed. Thereafter the liposome solution formed is immediately diluted with buffer solution to enhance homogeneity and maintain small particle size.

16 Claims, 6 Drawing Sheets

(56) References Cited

U.S. PATENT DOCUMENTS

| | | | |
|---|---|---|---|
| 6,007,838 | A | 12/1999 | Alving et al. |
| 6,093,348 | A | 7/2000 | Kowalski et al. |
| 6,596,305 | B1 * | 7/2003 | Edgerly-Plug ............... 424/450 |
| 6,835,395 | B1 | 12/2004 | Semple et al. |
| 6,843,942 | B2 | 1/2005 | Katinger et al. |
| 7,341,738 | B2 | 3/2008 | Semple et al. |
| 7,641,915 | B2 * | 1/2010 | Chen et al. ............... 424/450 |
| 8,329,070 | B2 | 12/2012 | MacLachlan et al. |
| 2003/0077829 | A1 | 4/2003 | MacLachlan |
| 2003/0124033 | A1 * | 7/2003 | Baker et al. ............... 422/128 |
| 2004/0032037 | A1 | 2/2004 | Katinger et al. |
| 2004/0037874 | A1 | 2/2004 | Hong et al. |
| 2004/0142025 | A1 | 7/2004 | MacLachlan et al. |
| 2006/0058249 | A1 * | 3/2006 | Tong et al. ............... 514/43 |
| 2008/0200417 | A1 | 8/2008 | Semple et al. |
| 2009/0191259 | A1 | 7/2009 | Li et al. |

FOREIGN PATENT DOCUMENTS

| | | | |
|---|---|---|---|
| CA | 2491164 | A1 | 1/2004 |
| EP | 0 055 576 | A | 7/1982 |
| EP | 0 055 576 | A1 | 7/1982 |
| EP | 1 013 268 | A | 6/2000 |
| EP | 1 013 268 | A1 | 6/2000 |
| EP | 1 203 614 | A | 5/2002 |
| EP | 1 203 614 | A1 | 5/2002 |
| IE | 911350 | | 7/1982 |
| IE | 911350 | | 4/1991 |
| WO | WO 89/07929 | A1 | 9/1989 |
| WO | WO 91/16039 | A1 | 10/1991 |
| WO | WO 96/40964 | A2 | 12/1996 |
| WO | WO 00 29103 | A | 5/2000 |
| WO | WO 00/29103 | A1 | 5/2000 |
| WO | WO 01 05373 | A | 1/2001 |
| WO | WO 01/05373 | A1 | 1/2001 |
| WO | WO 02 43699 | A | 6/2002 |
| WO | WO 02/43699 | A2 | 6/2002 |
| WO | 2004/002453 | * | 1/2004 |
| WO | WO 2004/002453 | A1 | 1/2004 |

OTHER PUBLICATIONS

Georgopapadakou, Nafsika H., "Drug Transport in Antimicrobial and Anticancer Chemotherapy," 1995, pp. 1-133, Marcel Dekker, Inc., New York City, New York, USA.

Isele et al. "Large-Scale Production of Lipsomes Containing Monomeric Zinc Phthalacyanine by Controlled Dilution of Organic Solvents" *Journal of Pharmaceutical Sciences*, Nov. 1994, vol. 83, No. 11, pp. 1608-1616.

Welter et al. "Simple Mixing Device to Reporducibly Prepare Catonic Lipid-DNA Complexes (Lipoplexes)", *BioTechniques*, Aug. 1999, vol. 27, pp. 286-290.

Jeffs, et al. "A Scalable, Extrusion-Free Method for Efficient Liposomal Encapsulation of Plasmid DNA" Pharmaceutical Research, 2005, vol. 22, No. 3 pp. 362-372.

Wagner, et al. "The Crossflow Injection Technique: An improvement of the Ethanol Injection Method," Journal of Liposome Research, 2002, vol. 12, No. 3, pp. 259-270.

Maurer et al. "Spontaneous Entrapment of Polynucleotides upon Electrostatic Interaction with Ethanol-Destabilized Cationic Liposomes," Biological Journal, May 2001, vol. 80, pp. 2310-2326.

"Drug Transport in Antimicrobial and Anticancer Chemotherapy." Nafsika H. Georgopapadakou ed., Marcel Dekker, Inc. (1995).

Batzri et al. "Single Bilayer Liposomes Prepred without Sonication," Biochimica et Biophysica acta 1973, vol. 298, pp. 1015-1019.

Hirota et al. "Simple Mixing Device to Reproducibly Prepare Catonic Lipid-DNA Complexes (Lipoplexes)", BioTechniques, Aug. 1999, vol. 27, No. 2, pp. 286-290.

Isele et al. "Large-Scale Production of Lipsomes Containing Monomeric Zinc Phthalocyanine by Controlled Dilution of Organic Solvents" Journal of Pharmaceutical Sciences, 1994, vol. 83, No. 11, pp. 1608-1616.

MacLachlan, Ian "Chapter 9; Liposomal Formulations for Nucleic Acid Delivery" Antisense Drug Technologies, Second Edition, Taylor and Francis Group, LLC, 2007, pp. 237-270.

Paul et al. "Effective expression of small interfering RNA in human cells," Nature Biotechnology, May 2002, vol. 20, pp. 505-508.

Semple et al. "Efficient encapsulation of antisense oligonucleotides in lipid vesicles using ionizable aminolipids: formation of novel small multilamellar vesicle structures," Biochim. et Biophys. Acta, 2001, vol. 1510, No. 1-2, pp. 152-166.

Szoka et al. "Comparative Properties and Methods of Preparation of Lipid Vesicles (liposomes)," Ann. Rev. Biophys. Bioeng. 1980, vol. 9, pp. 467-508.

Wheeler et al. "Stabilized plasmid-lipid particles: construction and characterization," Gene Ther., 1999, vol. 6, No. 2, pp. 271-281.

Zelphati et al. "Stable and Monodisperse Lipoplex Formulations for Gene Delivery," Gene Therapy, 1998, vol. 5, pp. 1272-1282.

\* cited by examiner

SYSTEMS AND METHODS FOR MANUFACTURING LIPOSOMES

CROSS-REFERENCES TO RELATED APPLICATIONS

This application is a non-provisional application claiming the benefit of U.S. Application No. 60/703,380, filed Jul. 27, 2005, entitled "SYSTEMS AND METHODS FOR MANUFACTURING LIPOSOMES," which is hereby incorporated by reference in its entirety.

BACKGROUND OF THE INVENTION

Many systems for administering active substances into cells are already known, such as liposomes, nanoparticles, polymer particles, immuno- and ligand-complexes and cyclodextrins (see, Drug Transport in antimicrobial and anticancer chemotherapy. G. Papadakou Ed., CRC Press, 1995). Liposomes are typically prepared in the laboratory by sonication, detergent dialysis, ethanol injection or dilution, French press extrusion, ether infusion, and reverse phase evaporation. Liposomes with multiple bilayers are known as multilamellar lipid vesicles (MLVs). MLVs are candidates for time release drugs because the fluids entrapped between layers are only released as each membrane degrades. Liposomes with a single bilayer are known as unilamellar lipid vesicles (UV). UVs may be made small (SUVs) or large (LUVs).

Some of the methods above for liposome production impose harsh or extreme conditions which can result in the denaturation of the phospholipid raw material and encapsulated drugs. In addition, these methods are not readily scalable for mass production of large volumes of liposomes. Further, lipid vesicle formation by conventional ethanol dilution, involves the injection or dropwise addition of lipid in an aqueous buffer. The resulting vesicles are typically heterogenous in size and contain a mixture of unilamellar and multilamellar vesicles.

Conventional liposomes are formulated to carry therapeutic agents either contained within the aqueous interior space (water-soluble drugs) or partitioned into the lipid bilayer(s) (water-insoluble drugs). Active agents which have short half-lives in the bloodstream are particularly suited to delivery via liposomes. Many anti-neoplastic agents, for example, are known to have a short half-life in the bloodstream such that their parenteral use is not feasible. However, the use of liposomes for site-specific delivery of active agents via the bloodstream is severely limited by the rapid clearance of liposomes from the blood by cells of the reticuloendothelial system (RES).

U.S. Pat. No. 5,478,860, which issued to Wheeler et al., on Dec. 26, 1995, and which is incorporated herein by reference, discloses microemulsion compositions for the delivery of hydrophobic compounds. Such compositions have a variety of uses. In one embodiment, the hydrophobic compounds are therapeutic agents including drugs. The patent also discloses methods for in vitro and in vivo delivery of hydrophobic compounds to cells.

PCT Publication WO01/05373 to Knopov et al., which is incorporated by reference herein, discloses techniques for preparing lipid vesicles using an ethanol injection-type process with a static mixer that provides a turbulent environment (e.g., Reynolds numbers>2000). Therapeutic agents may then be loaded after vesicle formation.

Published U.S. Application 2004/0142025, which is incorporated by reference herein, discloses techniques for forming lipid particles using a sequential stepwise dilution process. The process disclosed produces lipid particles having sizes below 200 nm in a non-turbulent mixing environment. However, the disclosed processes tend to result in less optimal vesicle sizes and less than optimal homogeneity, especially for liposomes encapsulating siRNA. Also, for encapsulated plasmids, an acidic buffer solution is required.

Despite the advances disclosed in U.S. Pat. No. 5,478,860, US20040142025 and WO 05373, there exists a need for improved processes and apparatus for formulating and producing lipid vesicles, and in particular lipid vesicles encapsulating a therapeutic agent such as nucleic acid. The present invention fulfills these and other needs.

BRIEF SUMMARY OF THE INVENTION

The present invention provides processes and apparatus for making lipid vesicles that optionally contain a therapeutic agent. The therapeutic agent can include, for example, a protein, a nucleic acid, an antisense nucleic acid, a drug, or the like. The present invention can be used to form lipid vesicles that contain encapsulated nucleic acid or small molecule drugs. In one aspect, the lipid vesicles are prepared rapidly at low pressure and the approach is fully scalable. In certain preferred embodiments, the process does not involve a static mixer or specialized extrusion equipment.

According to one embodiment, the present invention provides a method for producing a liposome. The process typically includes providing an aqueous solution in a first reservoir, the first reservoir in fluid communication with an organic lipid solution in a second reservoir, and mixing said aqueous solution with said organic lipid solution in a first mixing region to produce a liposome solution. The organic lipid solution mixes with said aqueous solution so as to substantially instantaneously produce a liposome encapsulating the therapeutic product. Immediately thereafter the liposome solution is mixed with a buffer solution to produce a diluted liposome solution. The liposome solution may be introduced to a buffer solution reservoir, or the liposome solution may be mixed with buffer in a second mixing region.

In certain aspects, the aqueous solution such as a buffer, comprises a therapeutic product, such that the therapeutic product is encapsulated in the liposome. In other aspects, the organic lipid solution includes a therapeutic product. Suitable therapeutic products include, but are not limited to, a protein, a nucleic acid, an antisense nucleic acid, a ribozyme, tRNA, snRNA, siRNA (small interfering RNA), shRNA, ncRNA, pre-condensed DNA, an aptamer and an antigen. In certain preferred aspects, the therapeutic product is nucleic acid.

In another embodiment, the present invention provides a system for producing a liposome encapsulating a therapeutic product. The system typically includes a first reservoir for holding an aqueous solution, and a second reservoir for holding an organic lipid solution, wherein one of the aqueous solution and the organic lipid solution includes a therapeutic product. The system also typically includes a pump mechanism configured to pump the aqueous solution and the organic lipid solution into a mixing region at substantially equal flow rates, wherein the organic lipid solution mixes with the aqueous solution in the mixing region to substantially instantaneously form a therapeutic product encapsulated liposome solution. The system further typically includes a collection reservoir, comprising a buffer solution, in fluid communication with the mixing region, wherein the liposome solution is introduced to the collection reservoir substantially immediately after formation, thereby forming a diluted liposome solution.

In yet another embodiment, the present invention provides a system for producing a liposome encapsulating a therapeutic product. The system typically includes a first reservoir for holding an aqueous solution, and a second reservoir for holding an organic lipid solution, wherein one of the aqueous solution and the organic lipid solution includes a therapeutic product. The system also typically includes a first pump mechanism configured to pump the aqueous solution and the organic lipid solution into a first mixing region at substantially equal flow rates, wherein the organic lipid solution mixes with the aqueous solution in the first mixing region to substantially instantaneously form a therapeutic product encapsulated liposome solution. The system also typically includes a buffer reservoir holding a buffer solution, and a second pump mechanism configured to pump the buffer solution into a second mixing region at a controlled flow rate, wherein the liposome solution is introduced to the second mixing region substantially immediately after formation in the first mixing region, thereby forming a diluted liposome solution in the second mixing region.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

I. Definitions

Figure 1:
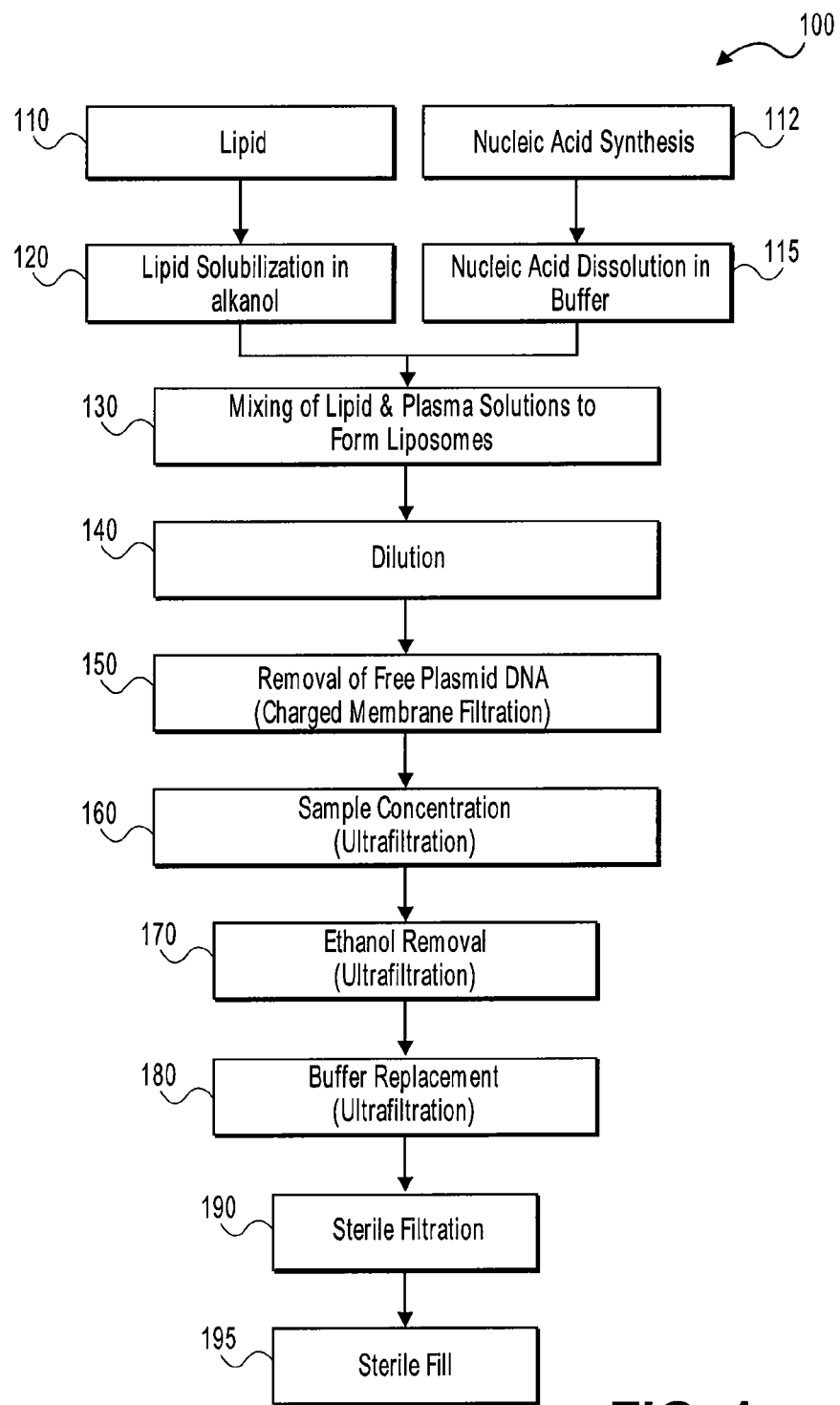
FIG. 1 illustrates a schematic for the process used to prepare SNALP

The term "nucleic acid" refers to a polymer containing at least two nucleotides. "Nucleotides" contain a sugar deoxyribose (DNA) or ribose (RNA), a base, and a phosphate group. Nucleotides are linked together through the phosphate groups (although synthetic nucleic acids may be prepared using nucleotide linkers other than phosphate groups). "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), shRNA (short-hairpin RNA), ncRNA (non-coding RNA), aptamers, ribozymes, chimeric sequences, or derivatives of these groups.

"Antisense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothioates, and other variants of the phosphate backbone of native nucleic acids. In addition, DNA and RNA may be single, double, triple, or quadruple stranded.

The term "gene" refers to a nucleic acid (e.g., DNA) sequence that comprises coding sequences necessary for the production of a polypeptide or precursor (e.g., herpes simplex virus). The polypeptide can be encoded by a full length coding sequence or by any portion of the coding sequence so long as the desired activity or functional properties (e.g., enzymatic activity, ligand binding, signal transduction, and the like) of the full-length or fragment are retained.

As used herein, the term "aqueous solution" refers to a composition comprising in whole, or in part, water.

As used herein, the term "organic lipid solution" refers to a composition comprising in whole, or in part, an organic solvent having a lipid.

The term "lipid" refers to a group of organic compounds that are esters of fatty acids and are characterized by being insoluble in water but soluble in many organic solvents. They are usually divided in at least three classes: (1) "simple lipids" which include fats and oils as well as waxes; (2) "compound lipids" which include phospholipids and glycolipids; (3) "derived lipids" such as steroids.

The term "amphipathic lipid" refers, in part, to any suitable material wherein the hydrophobic portion of the lipid material orients into a hydrophobic phase, while a hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids. Useful noncationic lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), and 1,2-dielaidoyl-sn-glycero-3-phophoethanolamine (trans-DOPE).

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species which carry a net positive charge at a selective pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). The following lipids are cationic and have a positive charge at below physiological pH: DODAP, DODMA, DMDMA, 1,2-DiLinoleyloxy-N,N-dimethylaminopropane (DLinDMA), 1,2-Dilinolenyloxy-N,N-dimethylaminopropane (DLenDMA), and the like.

In addition to cationic and non-cationic lipids, the SNALP of the present invention may comprise bilayer stabilizing component (BSC) such as an ATTA-lipid or a PEG-lipid, such as PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689, PEG coupled to phosphatidylethanolamine (PE) (PEG-PE), or PEG conjugated to ceramides, or a mixture thereof (see, U.S. Pat. No. 5,885,613). In one preferred embodiment, the BSC is a conjugated lipid that inhibits aggregation of the SNALP.

In certain aspects, the cationic lipid typically comprises from about 2% to about 70%, from about 5% to about 50%, from about 10% to about 45%, from about 20% to about 40%, or from about 30% to about 40% of the total lipid present in said particle. The non-cationic lipid typically comprises from about 5% to about 90%, from about 10% to about 85%, from about 20% to about 80%, from about 30% to about 70%, from about 40% to about 60% or about 48% of the total lipid present in said particle. The PEG-lipid conjugate typically comprises from about 0.5% to about 20%, from about 1.5% to about 18%, from about 4% to about 15%, from about 5% to about 12%, or about 2% of the total lipid present in said particle. The nucleic acid-lipid particles of the present invention may further comprise cholesterol. If present, the cholesterol typically comprises from about 0% to about 10%, about 2% to about 10%, about 10% to about 60%, from about 12% to about 58%, from about 20% to about 55%, or about 48% of the total lipid present in said particle. It will be readily apparent to one of skill in the art that the proportions of the components of the nucleic acid-lipid particles may be varied.

In some embodiments, the nucleic acid to lipid ratios (mass/mass ratios) in a formed nucleic acid-lipid particle will range from about 0.01 to about 0.2, from about 0.03 to about 0.01 or about 0.01 to about 0.08. The ratio of the starting materials also falls within this range. In another embodiment, the nucleic acid-lipid particle preparation uses about 400 μg nucleic acid per 10 mg total lipid or a nucleic acid to lipid ratio of about 0.01 to about 0.08, or about 0.04, which corresponds to 1.25 mg of total lipid per 50 μg of nucleic acid.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid, with a reduced aqueous interior; or lipid aggregates or micelles, wherein the encapsulated component is contained within a relatively disordered lipid mixture.

As used herein, "lipid encapsulated" can refer to a lipid formulation which provides a compound with full encapsulation, partial encapsulation, or both.

As used herein, the term "SNALP" refers to a stable nucleic acid lipid particle. A SNALP represents a vesicle of lipids coating an interior comprising a nucleic acid such as a plasmid with a reduced aqueous interior.

II. General

The present invention provides processes and apparatus for making lipid vesicles. The processes can be used to make lipid vesicles possessing a wide range of lipid components including, but not limited to, cationic lipids, anionic lipids, neutral lipids, polyethylene glycol (PEG) lipids, hydrophilic polymer lipids, fusogenic lipids and sterols. Hydrophobic actives can be incorporated into the organic solvent (e.g., ethanol) with the lipid, and nucleic acid and hydrophilic actives can be added to an aqueous component. In certain aspects, the processes of the present invention can be used in preparing microemulsions where a lipid monolayer surrounds an oil-based core. In certain aspects, the processes and apparatus are used in preparing lipid vesicles, or liposomes, wherein a therapeutic agent is encapsulated within a liposome coincident with liposome formation.

III. Processes of Making

FIG. 1 is an example of a representative flow chart 100 of a method of the present invention. This flow chart is merely an illustration and should not limit the scope of the claims herein. One of ordinary skill in the art will recognize other variations, modifications, and alternatives.

In one aspect, the present method provides a lipid solution 110 such as a clinical grade lipid synthesized under Good Manufacturing Practice (GMP), which is thereafter solubilized in an organic solution 120 (e.g., ethanol). Similarly, a therapeutic product, e.g., a therapeutic active agent such as nucleic acid 112 or other agent, is prepared under GMP. Thereafter, a therapeutic agent solution (e.g., nucleic acids) 115 containing a buffer (e.g., citrate) is mixed with a lipid solution 120 solubilized in a lower alkanol to form a liposomal formulation 130 (also referred to herein as "liposome suspension" or "liposome solution"). The therapeutic agent is entrapped in the liposome substantially coincident with formation of the liposome. Typically, an electrostatic interaction between the negatively charged nucleic acid and positively charged cationic lipid brings about encapsulation. If a titratable cationic lipid is used, for example, poor NA encapsulation efficiencies may be achieved at higher pH approaching or exceeding the cationic lipids pKa. Those of skill in the art will realize, however, that the processes and apparatus of the present invention are equally applicable to active entrapment or loading of the liposomes after formation of the vesicle. In certain aspects, the liposome solution is substantially immediately mixed with a buffer solution 140 to dilute the liposome solution (e.g., suspension of liposomes).

According to the processes and systems of the present invention, the action of continuously introducing lipid and buffer solutions into a mixing environment, such as in a mixing chamber, causes a continuous dilution of the lipid solution with the buffer solution, thereby producing a liposome substantially instantaneously upon mixing. Immediately diluting the liposome suspension, e.g., mixing the liposome suspension with buffer, helps prevent liposome particle sizes from increasing as would typically be the case if the liposome suspension is allowed to sit for an extended period of time, e.g., minutes or hours. Also, immediate dilution further enhances liposome homogeneity especially where siRNA is the encapsulated therapeutic agent. As used herein, the phrase "continuously diluting a lipid solution with a buffer solution" (and variations) generally means that the lipid solution is diluted sufficiently rapidly in an hydration process with sufficient force to effectuate vesicle generation.

In the processes of the present invention, the organic lipid solution typically includes an organic solvent, such as a lower alkanol. As mentioned above, in one aspect, the liposomes are immediately diluted 140 with a buffer (e.g., citrate) to increase nucleic acid (e.g., plasmid) entrapment and maintain particle size. Such dilution may be by way of immediate introduction of the liposome solution into a controlled amount of buffer solution, or by mixing the liposome solution with a controlled flow rate of buffer in a second mixing region. Before sample concentration 160, free therapeutic agent (e.g., nucleic acid) is removed by using, for example, an anion exchange cartridge 150. Further, by using an ultrafiltration step 170 to remove the alkanol, the sample is concentrated (e.g., to about 0.9 mg/mL plasmid DNA), the alkanol is removed, and the buffer is replaced with a substitute buffer (e.g., with a saline buffer) 180. Thereafter, the sample is filtered 190 and filled in vials 195. The process will now be discussed in more detail herein below using the steps as set forth in FIG. 1.

1. Lipid Solubilization and Therapeutic Agent Dissolution

In one embodiment, the liposome vesicles produced according to the processes of the present invention include stable nucleic acid lipid particle (i.e., SNALP) formulations.

Those of skill in the art will appreciate that the following description is for illustration purposes only. The processes of the present invention are applicable to a wide range of lipid vesicle types and sizes. These lipid vesicles include, but are not limited to, single bilayer lipid vesicles known as unilamellar lipid vesicles which can be made small (SUVs) or large (LUVs), as well as multilamellar lipid vesicles (MLVs). Further vesicles include, micelles, lipid-nucleic acid particles, virosomes, and the like. Those of skill in the art will know of other lipid vesicles for which the processes and apparatus of the present invention will be suitable.

The preferred size for liposomes made in accordance with the present processes and apparatus are between about 50-200 nm in diameter. In certain aspects, the liposome preparation has a size distribution in which the mean size (e.g., diameter) is about 70 nm to about 200 nm, and more typically the mean size is about 100 nm or less.

In certain aspects, the liposome formulation (e.g., SNALP formulation) of the present invention includes four lipid components: a phospholipid; cholesterol; a PEG-lipid; and a cationic lipid. In one aspect, the phospholipid is DSPC, the PEG-lipid is PEG-S-DSG and the cationic lipid is DODMA. In one aspect, the molar composition is about 20:45:10:25 DSPC:Chol:PEG-DSG:DODMA. In another aspect, the SNALP formulation is 20:48:2:30 DSPC:cholesterol:PEG-C-DMA:DlinDMA. In certain embodiments, the organic solvent concentration wherein the lipids are solubilized is about 45% v/v to about 100% v/v. In certain aspects, the organic solvent is a lower alkanol. Suitable lower alkanols include, but are not limited to, methanol, ethanol, propanol, butanol, pentanol, their isomers and combinations thereof. In one embodiment, the solvent is ethanol with a volume of about 50-90% v/v. In one aspect, the lipids occupy a volume of about 1 mL/g to about 5 mL/g.

The lipids are solubilized 120 using for example, an overhead stirrer at a suitable temperature. In one aspect, the total lipid concentration of the solution is about 15.1 (e.g., about 11.6 for a SNALP formulation) mg/mL (20 mM). In certain aspects, the therapeutic agent (e.g., nucleic acid) is included in an aqueous solution (e.g., buffer) and is diluted to a final concentration. In one aspect, for example, the final concentration is about 0.9 mg/mL in citrate buffer, with a pH of about 4-6. In this instance, the volume of the plasmid solution is the same as the alkanol-lipid solution. It should be appreciated that the buffer solution need not be acidic when using the direct dilution approaches of the present invention, e.g., the pH of the buffer solution can be 7.0 or higher. In one embodiment, the preparation of the therapeutic agent (e.g., nucleic acid) solution is performed in a jacketed stainless steel vessel with an overhead mixer. The sample does not need to be heated to be prepared, although in certain instances it is at the same temperature as the lipid solution prior to lipid vesicle formation.

In one embodiment, the therapeutic agent is included in the lipid solution. In certain aspects, the therapeutic agent in the lipid solution is lipophilic. Suitable lipophilic agents include taxol, taxol derivatives, including, for example, protax III and paclitaxol, lipophilic benzoporphyrins, verteporfin the lipid prodrug of foscarnet, 1-O-octadecyl-sn-glycerol-3-phosphonoformate (ODG-PFA), dioleoyl[3H]iododeoxyuridine ([3H]IDU-012), lipid derivatized HIV protease inhibitory peptides such as iBOC-[L-Phe]-[D-beta-NaI]-Pip-[alpha-(OH)-Leu]-Val (7194) and other lipid derivatized drugs or prodrugs.

2. Liposome Formation

After the solutions, e.g., lipid solution 120 and aqueous therapeutic agent (e.g., nucleic acid) solution 115, have been prepared, they are mixed together 130 using, for example, a peristaltic pump mixer or a pulseless gear pump. In one aspect, the solutions are pumped at substantially equal flow rates into a mixing environment, although non-equal flow rates may be used. In certain aspects, the mixing environment includes a "T"-shaped connector or mixing chamber. In this instance, it is preferred that the fluid lines, and hence fluid flows, meet in a narrow aperture within the "T"-connector as opposing flows at approximately 180° relative to each other. Other mixing chambers or connectors having shallower relative introduction angles may be used, such as for example between 27° and 90° and between 90° and 180°. Upon meeting and mixing of the solution flows in the mixing environment, lipid vesicles are substantially instantaneously formed. Lipid vesicles are formed when an organic solution including dissolved lipid and an aqueous solution (e.g., buffer) are simultaneously and continuously mixed. Advantageously, and surprisingly, by mixing the aqueous solution with the organic lipid solution, the organic lipid solution undergoes a continuous, sequential stepwise dilution to substantially instantaneously produce a liposome solution (suspension of liposomes). The pump mechanism(s) can be configured to provide equivalent or different flow rates of the lipid and aqueous solutions into the mixing environment which creates lipid vesicles in a high alkanol environment.

Advantageously, and surprisingly, the processes and apparatus for mixing of the lipid solution and the aqueous solution as taught herein provides for encapsulation of therapeutic agent in the formed liposome substantially coincident with liposome formation with an encapsulation efficiency of up to about 90%. Further processing steps as discussed herein can be used to further refine the encapsulation efficiency and concentration if desired.

In one embodiment, lipid vesicles form when lipids dissolved in an organic solvent (e.g., ethanol) are diluted in a stepwise manner by mixing with an aqueous solution (e.g., buffer). This controlled stepwise dilution is achieved by mixing the aqueous and lipid streams together in an aperture, such as a T-connector, and immediately thereafter diluting in a buffer solution. The resultant lipid, solvent and solute concentrations can be kept constant throughout the vesicle formation process if desired. In one aspect, lipid vesicles are formed having a mean diameter of less than about 150 nm, e.g., about 100 nm or less, which advantageously do not require further size reduction by high-energy processes such as membrane extrusion, sonication or microfluidization.

Figure 2:
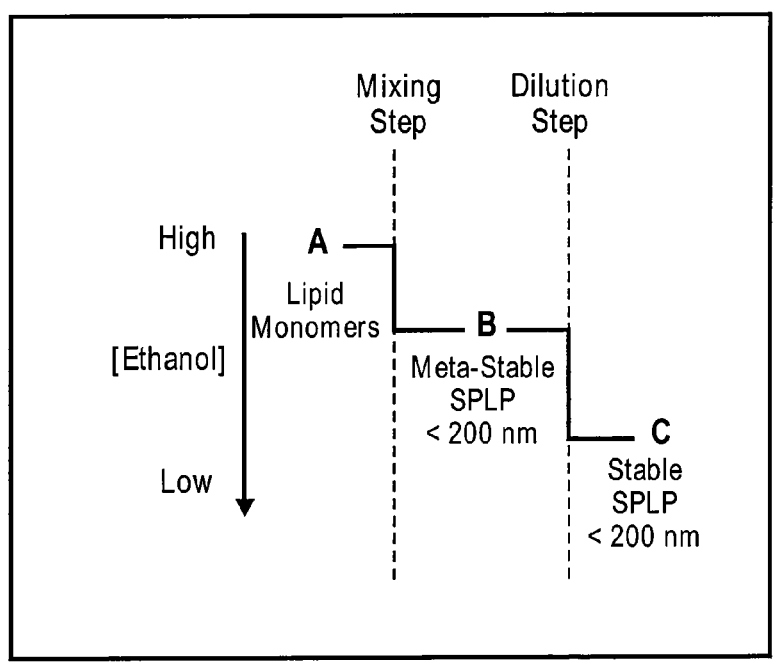
FIG. 2 provides a schematic of a process of making liposomes according to one embodiment of the present invention

One embodiment of the inventive process is shown in FIG. 2. In one aspect, using the processes of the present invention, a vesicle is prepared by a two-stage step-wise dilution without gradients. For example, in the first stepwise dilution, vesicles are formed in a high alkanol (e.g., ethanol) environment (e.g., about 20% to about 55% v/v ethanol). These vesicles can then be stabilized by lowering the alkanol (e.g., ethanol) concentration to less than or equal to about 25% v/v, such as about 17% v/v to about 25% v/v, in a stepwise manner. In certain aspects, with therapeutic agent present in the aqueous solution, or in the lipid solution, the therapeutic agent is encapsulated coincident with liposome formation.

As shown in FIG. 2, in one embodiment, lipids are initially dissolved in an alkanol environment of about 40% v/v to about 100% v/v, more typically about 65% v/v to about 90% v/v, and most typically about 80% v/v to about 90% v/v (A). Next, the lipid solution is diluted stepwise by mixing with an aqueous solution resulting in the formation of vesicles at an alkanol (e.g., ethanol) concentration of between about 20.0-55% (B). By mixing the aqueous solution with the organic lipid solution, the organic lipid solution undergoes a continuous, sequential stepwise dilution to produce a liposome. Further, lipid vesicles such as SNALP (a lipid-particle) can be further stabilized by an additional stepwise dilution of the vesicles to an alkanol concentration of less than or equal to about 25%, preferably between about 19-25% (C). In certain aspects, the additional sequential dilution (C) is performed substantially immediately after formation of the liposomes. For example, it is advantageous that less than 1 minute elapse between liposome solution formation and dilution (C), more advantageously less than 10 seconds and even more advantageously less than a second or two.

In certain aspects, for both sequential dilutions (A→B and B→C), the resulting ethanol, lipid and solute concentrations are kept at constant levels in the receiving vessel. At these higher ethanol concentrations following the initial mixing step, the rearrangement of lipid monomers into bilayers proceeds in a more orderly fashion compared to vesicles that are formed by dilution at lower ethanol concentrations. Without being bound by any particular theory, it is believed that these higher ethanol concentrations promote the association of nucleic acid with cationic lipids in the bilayers. In one aspect, nucleic acid encapsulation occurs within a range of alkanol (e.g., ethanol) concentrations above 22%.

In one aspect, the lipid vesicles are formed at a rate of 60 to about 400 mL/min. After the mixing step 130, the lipid concentration is about 1-12 mg/mL and the therapeutic agent (e.g., nucleic acid) concentration is about 0.05-0.23 mg/mL. In certain preferred aspects, the lipid concentration is about 1.25 mM 0.72 mg/mL and the therapeutic agent (e.g., nucleic acid) concentration is about 0.06 mg/mL to give a lipid:nucleic acid ratio of about 12. The buffer concentration is about 1-3 mM and the alkanol concentration is about 45% v/v to about 90% v/v. In preferred aspects, the buffer concentration is about 3 mM and the alkanol concentration is about 45% v/v to about 60% v/v.

3. Liposome Dilution

Turning back to FIG. 1, after the vesicle formation step 130, the degree of therapeutic agent (e.g., nucleic acid) encapsulation is enhanced and particle size maintained, and even reduced, by immediate diluting 140 the lipid vesicle suspension (liposome solution) prior to removal of free nucleic acid. For example, prior to dilution step 140, if the therapeutic agent entrapment is at about 50-60%, it can be increased to about 80-90% following dilution step 140. In step 140, the liposome formulation is diluted to about 10% to about 40%, preferably about 20% alkanol, by mixing with an aqueous solution such as a buffer (e.g., 1:1 with 20 mM citrate buffer, 300 mM NaCl, pH 6.0). The diluted sample is then optionally allowed to incubate at room temperature.

4. Removal of Free Therapeutic Agent

After immediate dilution 140, about 70-80% or more of the therapeutic agent (e.g., nucleic acid) is entrapped within the lipid vesicle (e.g., SNALP) and the free therapeutic agent can be removed from the formulation 150. In certain aspects, anion exchange chromatography is used. Advantageously, the use of an anion exchange resin results in a high dynamic nucleic acid removal capacity, is capable of single use, may be pre-sterilized and validated, and is fully scaleable. In addition, the method results in removal of free therapeutic agent (e.g., nucleic acid such as approximately 25% of total plasmid). The volume of sample after chromatography is unchanged, and the therapeutic agent (e.g., nucleic acid) and lipid concentrations are about 0.04-0.05 and 0.7 mg/mL, respectively. At this point, the sample can be assayed for encapsulated therapeutic agent.

5. Sample Concentration

In certain instances, the liposome solution is optionally concentrated about 5-50 fold, preferably 10-20 fold, using for example, ultrafiltration 160 (e.g., tangential flow dialysis). In one embodiment, the sample is transferred to a feed reservoir of an ultrafiltration system and the buffer is removed. The buffer can be removed using various processes, such as by ultrafiltration. In one aspect, buffer is removed using cartridges packed with polysulfone hollow fibers, for example, having internal diameters of about 0.5 mm to about 1.0 mm and a 30,000 nominal molecular weight cut-off (NMWC). Hollow fibers with about a 1,000 MWCO to about a 750,000 MWCO may also be used. The liposomes are retained within the hollow fibers and recirculated while the solvent and small molecules are removed from the formulation by passing through the pores of the hollow fibers. In this procedure, the filtrate is known as the permeate solution. On completion of the concentration step, the therapeutic agent (e.g., nucleic acid) and lipid concentrations can increase to about 2 and 60 mg/mL, respectively. In one embodiment, the alkanol concentration remains unchanged, but the alkanol:lipid ratio decreases about 50 fold.

6. Alkanol Removal

In one embodiment, the concentrated formulation is diafiltrated against about 5-20 volumes, preferably about 10 volumes, of aqueous solution (e.g., buffer) (e.g., citrate buffer pH 4.0 (25 mM citrate, 100 mM NaCl) to remove the alkanol 170. A neutral buffer or a sugar-based buffer may also be used. The alkanol concentration at the completion of step 170 is less than about 1%. Lipid and therapeutic agent (e.g., nucleic acid) concentrations remain unchanged and the level of therapeutic agent entrapment also remains constant.

7. Buffer Replacement

After the alkanol has been removed, the aqueous solution (e.g., buffer) is then replaced by dialfiltration against another buffer 180 (e.g., against 10 volumes of saline 150 mM NaCl with 10 mM Hepes or Phosphate pH 7.4). Any of a variety of buffers may be used, e.g., neutral, sugar-based, etc. Typically, the ratio of concentrations of lipid to therapeutic agent (e.g., nucleic acid) remain unchanged and the level of nucleic acid entrapment is about constant. In certain instances, sample yield can be improved by rinsing the cartridge with buffer at about 10% volume of the concentrated sample. In certain aspects, this rinse is then added to the concentrated sample.

8. Sterile Filtration

In certain preferred embodiments, sterile filtration 190 of the sample at lipid concentrations of about 12-120 mg/mL can optionally be performed. In certain aspects, filtration is conducted at pressures below about 40 psi, using a capsule filter and a pressurized dispensing vessel with a heating jacket. Heating the sample slightly can improve the ease of filtration.

9. Sterile Fill

The sterile fill step 195 is performed using similar processes as for conventional liposomal formulations. The processes of the present invention result in about 50-60% of the input therapeutic agent (e.g., nucleic acid) in the final product. In certain aspects, the therapeutic agent to lipid ratio of the final product is approximately 0.01 to 0.2.

IV. Therapeutic Agents

The lipid-based drug formulations and compositions of the present invention are useful for the systemic or local delivery of therapeutic agents or bioactive agents and are also useful in diagnostic assays. The following discussion refers generally to liposomes; however, it will be readily apparent to those of skill in the art that this same discussion is fully applicable to the other drug delivery systems of the present invention.

As described above, therapeutic agent is preferably incorporated into the lipid vesicle during formation of the vesicle. In one embodiment, hydrophobic actives can be incorporated into the organic solvent with the lipid, while nucleic acid and hydrophilic therapeutic agents can be added to the aqueous component. In certain instances, the therapeutic agent includes one of a protein, a nucleic acid, an antisense nucleic acid, ribozymes, tRNA, snRNA, siRNA, shRNA, ncRNA, pre-condensed DNA, an aptamer, an antigen and combinations thereof. In preferred aspects, the therapeutic agent is nucleic acid. The nucleic acid may encode a protein such as, for example, a herpes simplex virus, thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, or cytochrome P450 2B1.

In certain aspects, therapeutic agent is incorporated into the organic lipid component. In certain instances, the therapeutic agent is lipophilic. Suitable lipophilic agents include taxol, taxol derivatives, including, for example, protax III and Paclitaxol, lipophilic benzoporphyrins, verteporfin the lipid prodrug of foscamet, 1-O-octadecyl-sn-glycerol-3-phosphonoformate (ODG-PFA), dioleoyl[3H]iododeoxyuridine ([3H]IDU-012), lipid derivatized HIV protease inhibitory peptides such as iBOC-[L-Phe]-[D-beta-NaI]-Pip-[alpha-(OH)-Leu]-Val (7194) and other lipid derivatized drugs or prodrugs.

In another embodiment, the lipid vesicles of the present invention can be loaded with one or more therapeutic agents after formation of the vesicle. In certain aspects, the therapeutic agents which are administered using the present invention can be any of a variety of drugs which are selected to be an appropriate treatment for the disease to be treated. Often the drug is an antineoplastic agent, such as vincristine, doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues by the present processes. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-conversants, e.g., phenyloin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

V. Apparatus

Figure 3A:
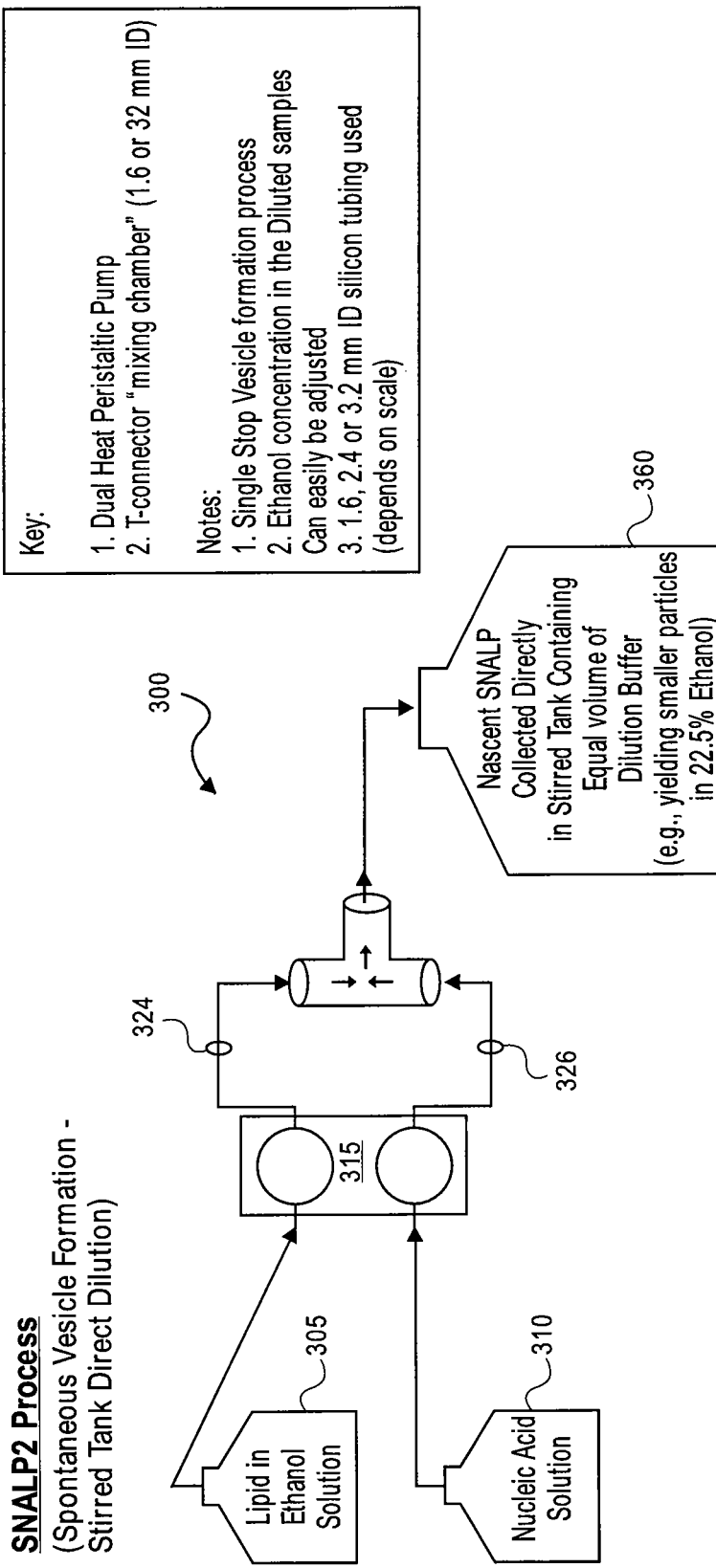
FIGS. 3a and 3b show examples of an apparatus 300 and apparatus 302, respectively, according to two embodiments of the present invention.
Figure 3B:
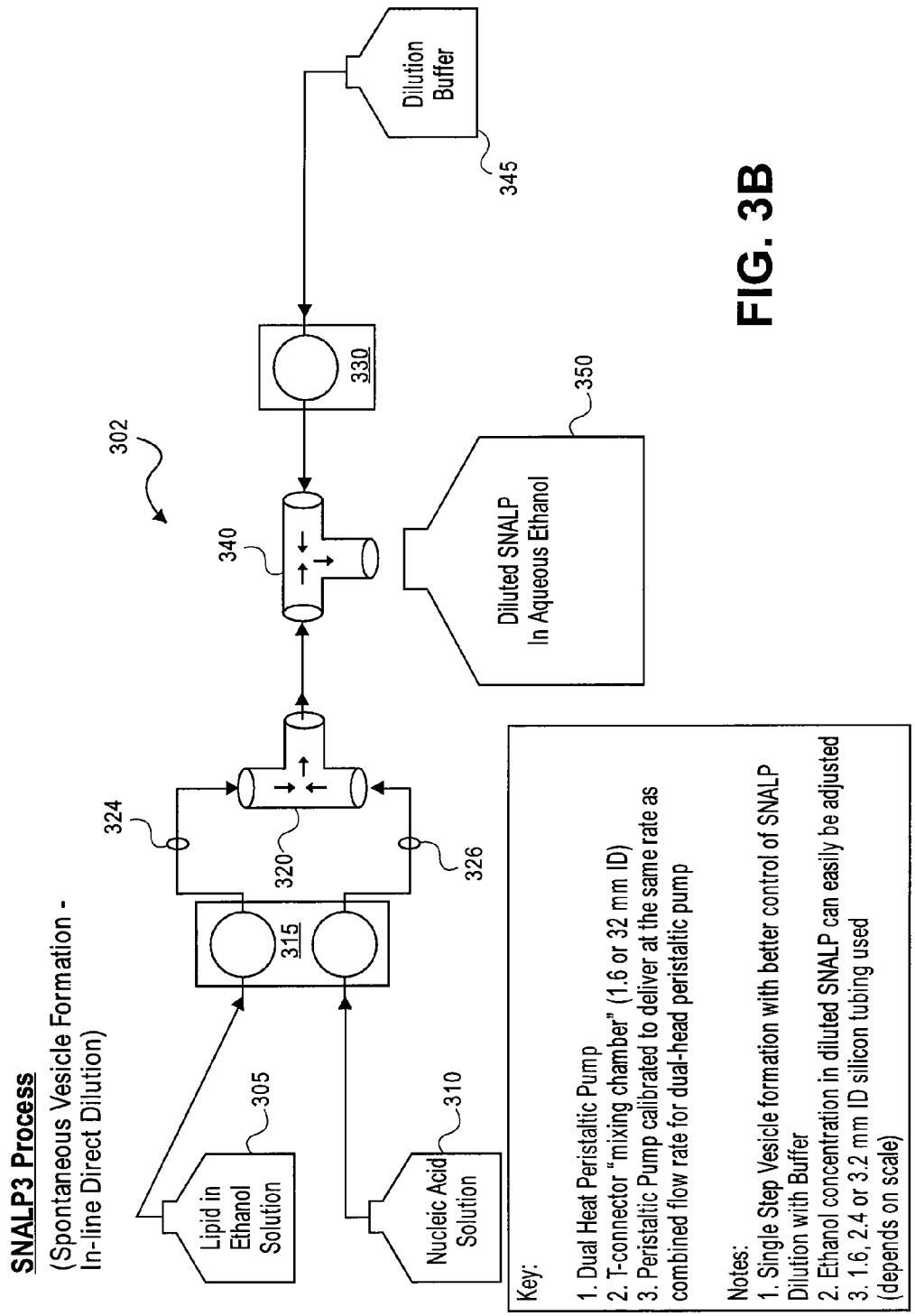

In one embodiment, the present invention provides systems and apparatus for carrying out the processes of the present invention. FIGS. 3*a* and 3*b* show examples of an apparatus 300 and apparatus 302, respectively, according to two embodiments of the present invention. These schematics are merely illustrations and should not limit the scope of the claims herein. One of ordinary skill in the art will recognize other variations, modifications, and alternatives.

As shown, apparatus 300 and apparatus 302 each includes two reservoirs, an aqueous solution reservoir 305 and an organic solution reservoir 310, for holding aqueous solution and organic solution, respectively. In certain aspects, the lipid vesicle formulations are prepared rapidly, at low pressure (e.g., <10 psi) and the apparatus and processes of the present invention are fully scaleable (e.g., 0.5 mL-5000 L). At a 1-L scale, lipid vesicles are formed at about 0.4-0.8 L/min. In certain preferred aspects, the apparatus does not use static mixers nor specialized extrusion equipment.

The mixing chamber 320 includes, in one embodiment, a T-connector, having optional hose barbs, wherein fluid lines 324 and 326 impact each other at about 180°. The angle of mixing can also be changed, and lipid vesicles less than about 100 nm can be formed at angles of between about 90° and about 180° or even between 27° and about 90°. In certain aspects, lipid vesicles of well defined and reproducible mean diameters are prepared using substantially equal flow rates of the flow lines. In other aspects, lipid vesicles of well defined and reproducible mean diameters are prepared by changing the flow rate of the fluid lines, e.g., to ensure sufficient mixing in some cases. In certain aspects, the variance between flow rates is less that 50%, more typically less than about 25% and even more typically less than about 5%.

Figure 5:
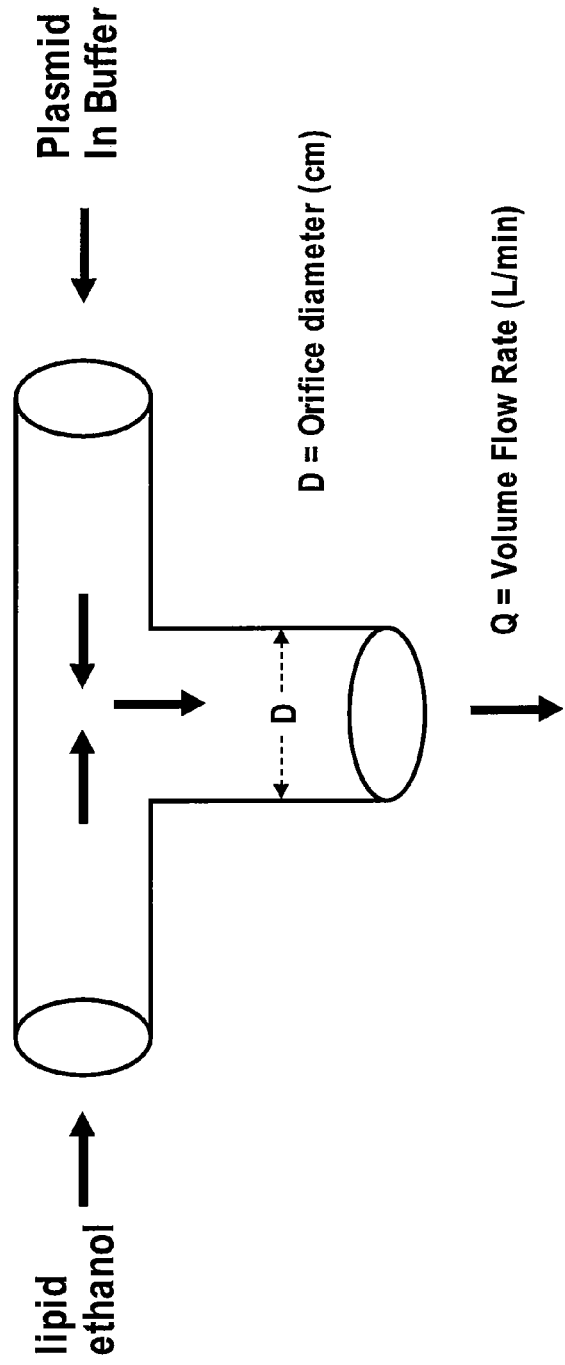
FIG. 5 shows a T-shaped connector and associated flow dynamics according to one embodiment.

FIG. 5 shows a T-connector and associated flow dynamics according to one embodiment. Examples of flow rates are shown and discussed in the Example section (below) in more detail. In comparison with prior systems, the present invention provides non-turbulent flow and increased shear rates at much lower (and substantially equivalent) flow rates. For example, the present invention advantageously provides non-turbulent flow ($N_{re}$<2000) in the mixing environment with a shear rate between about 500/s and about 3300/s at a flow rate (both flow lines) of between about 0.075 and about 0.4 L/min. These values are calculated for the tube downstream of the mixing chamber; it is difficult to predict what happens at the point of mixing in the T-connector. Turbulent flow may be created, but only at the point of mixing in the mixing chamber.

Mixing of the two fluid components can be driven using, for example, a peristaltic pump 315, a positive displacement pump, a pulseless gear pump, by pressurizing both the lipid-ethanol and buffer vessels 305, 310, or by a combination of two or more of these and/or other pump mechanisms. In one aspect, a Watson-Marlow 505Di/L pump fitted with a 505L pump head is used; silicone tubing (e.g., platinum cured with 3.2 mm ID, 2.4 mm wall thickness; available from Watson Marlow as catalog no. 913A032024) can be used for flow lines into a polypropylene or stainless steel T-connector (e.g., with a ⅛" ID). Lipid vesicles are typically formed at room temperature, but lipid vesicles may be formed at elevated temperatures according to the present invention. Unlike other existing approaches, there are no general requirements for buffer composition. In fact, the processes and apparatus of the present invention can formulate a lipid vesicle by mixing lipid in an alkanol with water. In certain aspects, the processes and apparatus of the present invention form lipid vesicles that are less than about 100 nm in diameter.

When lipid vesicles are prepared containing nucleic acid (such as SNALP), the ratio of nucleic acid to cationic lipid and counter ions can be optimized. For refined formulations, 70-95% nucleic acid ("NA") encapsulation after mixing, and ethanol removal steps is preferred. The level of NA encapsulation is advantageously increased by immediately diluting this initial SNALP formulation. Surprisingly, the processes and apparatus of the present invention provide an encapsulation efficiency, upon mixing the solutions (with therapeutic agent in one of the solution components) in the mixing environment, of up to about 90%. Two alternate embodiments of dilution, e.g., direct dilution, are shown in FIGS. 3a and 3b.

In the embodiment shown in FIG. 3a, the liposome solution formed in mixing region 320 is immediately and directly introduced into a collection vessel 360 containing a controlled amount of dilution buffer. In preferred aspects, vessel 360 includes one or more elements configured to stir the contents of vessel 360 to facilitate dilution. In one aspect, the amount of dilution buffer present in vessel 360 is substantially equal to the volume of liposome solution introduced thereto. As an example, liposome solution in 45% ethanol when introduced into vessel 360 containing an equal volume of ethanol will advantageously yield smaller particles in 22.5% ethanol.

In the embodiment shown in FIG. 3b, a third reservoir 345 containing dilution buffer is fluidly coupled to a second mixing region 340. In this embodiment, the liposome solution formed in mixing region 320 is immediately and directly mixed with dilution buffer in the second mixing region 340. In certain aspects, mixing region 340 includes a T-connector arranged so that the liposome solution and the dilution buffer flows meet as opposing 180° flows, however, connectors providing shallower angles can be used, e.g., 27° to about 180°. A pump mechanism 330 delivers a controllable flow of buffer to mixing region 340. In one aspect, the flow rate of dilution buffer provided to mixing region 340 is controlled to be substantially equal to the flow rate of liposome solution introduced thereto from mixing region 320. This embodiment advantageously allows for more control of the flow of dilution buffer mixing with the liposome solution in the second mixing region 340, and therefore also the concentration of liposome solution in buffer throughout the second mixing process. Such control of the dilution buffer flow rate advantageously allows for small particle size formation at reduced concentrations. See, e.g., the Examples section below.

In certain aspects, liposome producing apparatus 300 and 302 of the present invention further includes a temperature control mechanism (not shown) for controlling the temperature of the reservoirs 305 and 310. Typically, fluid from the first reservoir 305 and the second reservoirs 310 flows into mixing chamber 320 simultaneously at separate apertures. Apparatus 302 further includes a collection reservoir 350 downstream of the second mixing chamber 340 for liposome collection. Moreover, in certain aspects, apparatus 300 and 302 further include storage vessels upstream of either or both of the reservoirs 305 and 310. Further, either or both of the reservoirs 305 and 310 can include jacketed stainless steel vessels equipped with an overhead mixer.

Figure 4:
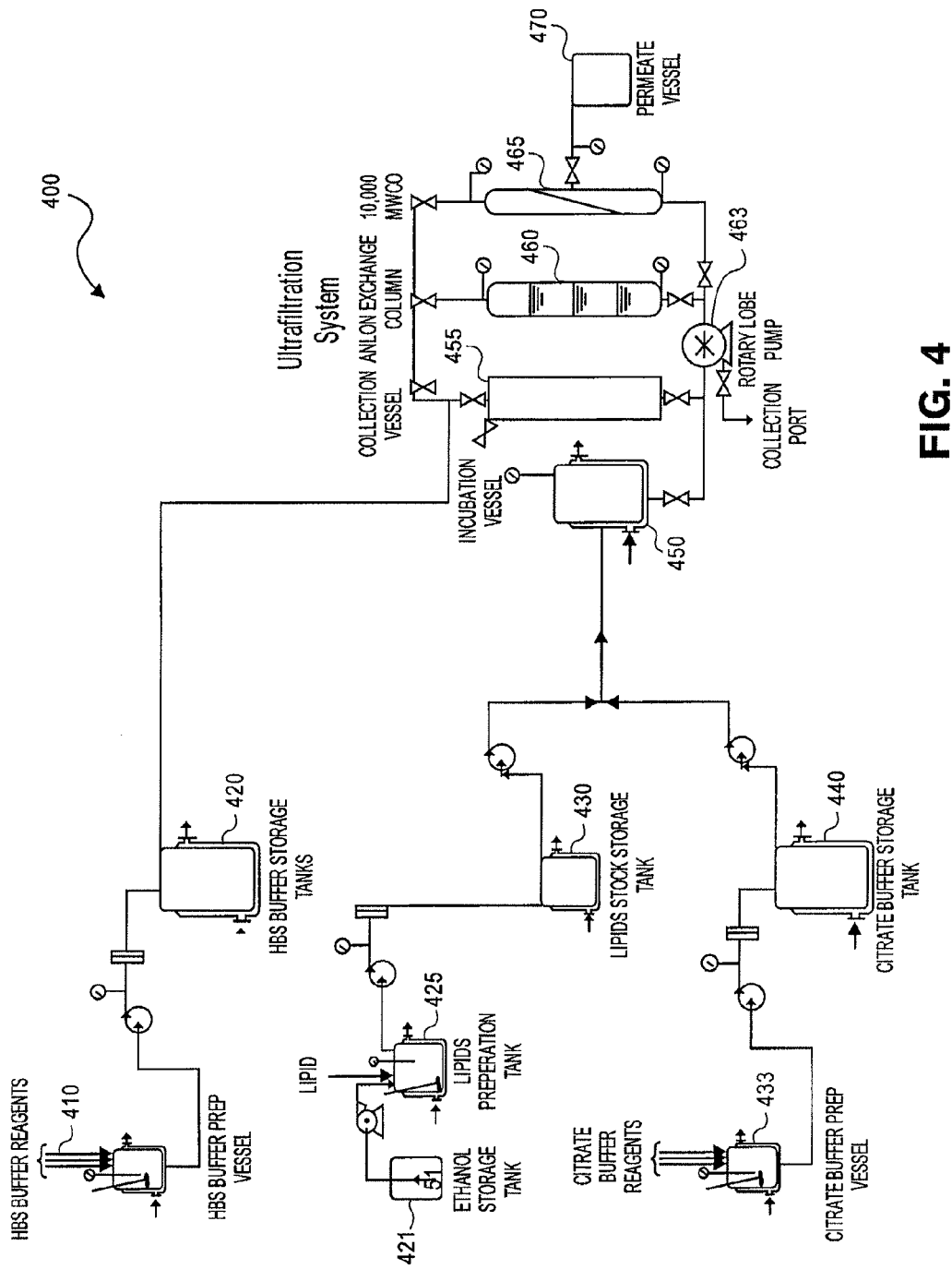
FIG. 4 is an example of a representative schematic of an apparatus 400 according to one embodiment of the present invention.

In another embodiment, the present invention provides an apparatus having an ultrafiltration system for carrying out the processes of the present invention. FIG. 4 is an example of a representative schematic of an apparatus 400 according to one embodiment of the present invention. This schematic is merely an illustration and should not limit the scope of the claims herein. One of ordinary skill in the art will recognize other variations, modifications, and alternatives.

In certain aspects, apparatus 400 includes a plurality of reservoirs and is equipped with an ultrafiltration system. An aqueous solution reservoir 440 and an organic solution reservoir 430 each have upstream preparation vesicles (not shown), respectively.

As shown in FIG. 4, the a collection vessel 450 is in fluid communication with the flow ultrafiltration system. In certain aspects, ultrafiltration is used to concentrate SNALP samples and then remove ethanol from the formulation by buffer replacement. It should be appreciated that collection vessel 450 can include a desired amount of dilution buffer when the process according to FIG. 3a is followed. Similarly, vessel 450 can act as collection vessel 350 of FIG. 3b, when the process according to FIG. 3b is followed (second pump not shown in FIG. 4).

In one embodiment of operation, the diluted SNALP are transferred to the feed reservoir of the ultrafiltration system. Concentration is performed by removing buffer and ethanol using, for example, cross flow cartridges 465 packed with polysulfone hollow fibers that possess internal diameters of about 0.5 mm to about 1.0 mm and about 1,000 to about 750,000 molecular weight cut-off (MWCO). The SNALP are retained within the hollow fibers and re-circulated, whereas the ethanol and buffer components are removed from the formulation by passing through the pores of these hollow fibers. This filtrate is known as the permeate solution and is discarded. After the SNALP are concentrated to the desired plasmid concentration, the buffer in which the SNALP are suspended may be removed by ultrafiltration and replaced by an equal volume of the final buffer. Ultrafiltration can be replaced with other methods such as conventional dialysis.

VI. Examples

Example 1

Comparison of Prior Method with Direct Dilution Process

SNALP are composed of 2 mol % PEG-C-DMA, 30% DlinDMA, 20 mol % DSPC and 48 mol % Chol"
WATSON MARLOW PUMP—MODEL 505 Di/L:
→Nucleic Acid: unmodified siRNA (re-constituted in 0.9% NaCl) (0.225 mg/ml siRNA)
→Mixing Volumes: 10 mL of nucleic acid+10 mL of lipid-ethanol solution (5 mM lipid)
→1.6 mm tee connector, 3.2 mm tubing, 40 cm tubing length per channel
→Flow Rate: 200 mL/min
Conditions:
1. Mixed nucleic acid with lipid, then diluted SNALP using pump after incubation delay (prior method).
2. Mixed nucleic acid with lipid, then diluted SNALP using pipette to add buffer
3. Mixed nucleic acid with lipid directly into a bottle containing dilution buffer (FIG. 3a with no stirring).
4. Mixed nucleic acid with lipid directly in Stirred dilution buffer (FIG. 3a).
Results:

|  | Parameter | | | |
| --- | --- | --- | --- | --- |
|  | 1 | 2 | 3 | 4 |
| Encapsulation (%) | 78.5 | 82.6 | 79.7 | 79.9 |
| Vesicle Size (nm) | 103.0 | 91.0 | 80.1 | 82.3 |
|  | (0.09) | (0.07) | (0.13) | (0.13) |

The direct dilution approach (FIG. 3a) produces significantly smaller SNALP particles with similar encapsulation efficiencies compared to SNALP prepared with the prior processes such as the process disclosed in Published U.S. Application 2004/0142025.

Example 2

Comparison of Processes of Present Invention Using Varying Process Parameters

Formation of 4× Concentrated SNALP
Process
SNALP2 shown in FIG. 3a
Process
SNALP 3 shown in FIG. 3b

| Condition | siRNA Solution | Lipid Solution | Dilution Buffer | Flow Rate (ml/min) | Encapsulation (%) | Size(nm) with poly |
| --- | --- | --- | --- | --- | --- | --- |
| SNALP2 | 0.225 mg/ml pH 5 | 5 mM 90% EtOH | 20 mM Citrate & 300 mM NaCl, pH 6 | 200 | 81.8 | 82.9 (0.15) |
| SNALP2 | 0.225 mg/ml pH 5 | 5 mM 90% EtOH | 20 mM Citrate & 300 mM NaCl, pH 6 | 400 | 82.1 | 75.2 (0.11) |
| 4× Concentrated SNALP2 | 0.9 mg/ml pH 5 | 20 mM 90% EtOH | 20 mM Citrate & 300 mM NaCl, pH 6 | 200 | 80.8 | 104.0 (0.14) |
| 4× Concentrated SNALP2 | 0.9 mg/ml pH 5 | 20 mM 90% EtOH | 20 mM Citrate & 300 mM NaCl, pH 6 | 400 | 80.9 | 112.4 (0.21) |
| 4× Conc. SNALP2 modified | 0.9 mg/ml pH 4 | 20 mM 100% EtOH | 20 mM PBS, pH 7 | 200 | 81.3 | 100.7 (0.14) |
| 4× Conc. SNALP2 modified | 0.9 mg/ml pH 4 | 20 mM 100% EtOH | 20 mM PBS, pH 7 | 400 | 81.1 | 98.9 (0.21) |

| Formation of 4× Concentrated SNALP Direct Dilution (FIG. 3a) vs In-line Dilution (FIG. 3b) | | | | | | |
| --- | --- | --- | --- | --- | --- | --- |
| Condition | siRNA Solution | Lipid Solution | Dilution Buffer | Flow Rate (ml/min)* | Encapsulation (%) | Size(nm) with poly |
| SNALP2 (4×) Direct Dilution | 0.9 mg/ml pH 4 | 20 mM 100% EtOH | 20 mM PBS, pH 7 | 400 | 80.2 | 88.4 (0.13) |
| SNALP3 In-line dilution |  |  | 20 mM PBS, pH 7 |  | 82.9 | 78.9 (0.12) |

*Flow rate value for the rate of initial vesicle formation prior to dilution, Dilution buffer delivered at 600 mL/min for In-line dilution method to achieve 20% EtOH in resultant SNALP sample.

Summary:
1. SNALP can be prepared at higher initial lipid and siRNA concentrations (4×) when pump flowrate is increased and modifications are made to the siRNA solution, the Lipid solution and Dilution buffer. These SNALP possess good encapsulation efficiencies and particle sizes.
2. Using a in-line Dilution approach (SNALP3—FIG. 3b), the particle sizes of these SNALP particles can be further controlled, giving particles that are similar in size to SNALP2 (FIG. 3a) prepared at a quarter of the initial lipid and siRNA concentrations.

VII. Conclusion

Additional features, advantages and examples of lipid particles that may be produced using the systems and methods of the present invention can be found in U.S. provisional patent application Ser. No. 60/703,226, titled "siRNA Silencing of Apoliprotein B", filed concurrently with this application on Jul. 27, 2005, the contents of which are hereby incorporated by reference. All patents, patent application and other references discussed herein are hereby incorporated by reference.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of producing a lipid vesicle encapsulating a therapeutic product, said method comprising:
   providing an aqueous solution in a first reservoir;
   providing an organic lipid solution in a second reservoir, wherein one of the aqueous solution and the organic lipid solution includes a therapeutic product;
   mixing said aqueous solution with said organic lipid solution in a first mixing region to produce a lipid vesicle solution, wherein said organic lipid solution mixes with said aqueous solution so as to substantially instantaneously produce a lipid vesicle encapsulating the therapeutic product, wherein mixing includes introducing the aqueous solution and the organic lipid solution into the first mixing region at substantially equal flow rates, wherein the first mixing region includes a first T-connector, and wherein the aqueous solution and the organic lipid solution are introduced into the first T-connector as opposing flows at substantially 180° relative to each other; and
   mixing said lipid vesicle solution with a buffer solution to produce a diluted lipid vesicle solution, wherein mixing said lipid vesicle solution with the buffer solution includes mixing in a second mixing region, wherein the lipid vesicle solution formed in the first mixing region is immediately and directly diluted with the buffer solution in the second mixing region less than two seconds after the lipid vesicle solution is formed, wherein the second mixing region includes a second T-connector, wherein the lipid vesicle solution and the buffer solution are introduced into the second T-connector at about 27° to about 180° relative to each other, and wherein the lipid vesicle is less than 100 nm in diameter.

2. The method of claim 1, wherein said lipid vesicle solution has a concentration of about 20% v/v to about 55% v/v organic solvent.

3. The method of claim 2, wherein the diluted lipid vesicle solution has a concentration of less than about 25% v/v organic solvent.

4. The method of claim 1, wherein said therapeutic product is selected from the group consisting of a protein, a plasmid, an aptamer, a nucleic acid, an antisense nucleic acid, a ribozyme, tRNA, snRNA, siRNA, shRNA, ncRNA, pre-condensed DNA and an antigen.

5. The method of claim 1, wherein said therapeutic product is a nucleic acid.

6. The method of claim 1, wherein said therapeutic product is an siRNA.

7. The method of claim 1, wherein said lipid vesicle is a stable nucleic acid-lipid particle (SNALP).

8. The method of claim 1, wherein the lipids present in said organic lipid solution are solubilized in an organic solvent.

9. The method of claim 8, wherein the organic solvent comprises a lower alkanol.

10. The method of claim 9, wherein said lower alkanol is selected from the group consisting of methanol, ethanol, propanol, butanol, pentanol, isomers thereof, and combinations thereof.

11. The method of claim 9, wherein said lower alkanol comprises 100% v/v ethanol.

12. The method of claim 1, wherein the lipids present in said organic lipid solution comprise a phospholipid, cholesterol, a PEG-lipid, and a cationic lipid.

13. The method of claim 1, wherein the aqueous solution includes said therapeutic product.

14. The method of claim 12, wherein the aqueous solution has a pH of about 4 to about 6.

15. The method of claim 2, wherein the diluted lipid vesicle solution has a concentration of about 17% v/v to about 25% v/v organic solvent.

16. The method of claim 1, wherein the lipid vesicle solution formed in the first mixing region is immediately and directly diluted with the buffer solution in the second mixing region less than one second after the lipid vesicle solution is formed.

* * * * *